Feb. 11, 1975 C. G. KLEHM Plant Pat. 3,684
PEONY PLANT
Filed Oct. 26, 1973
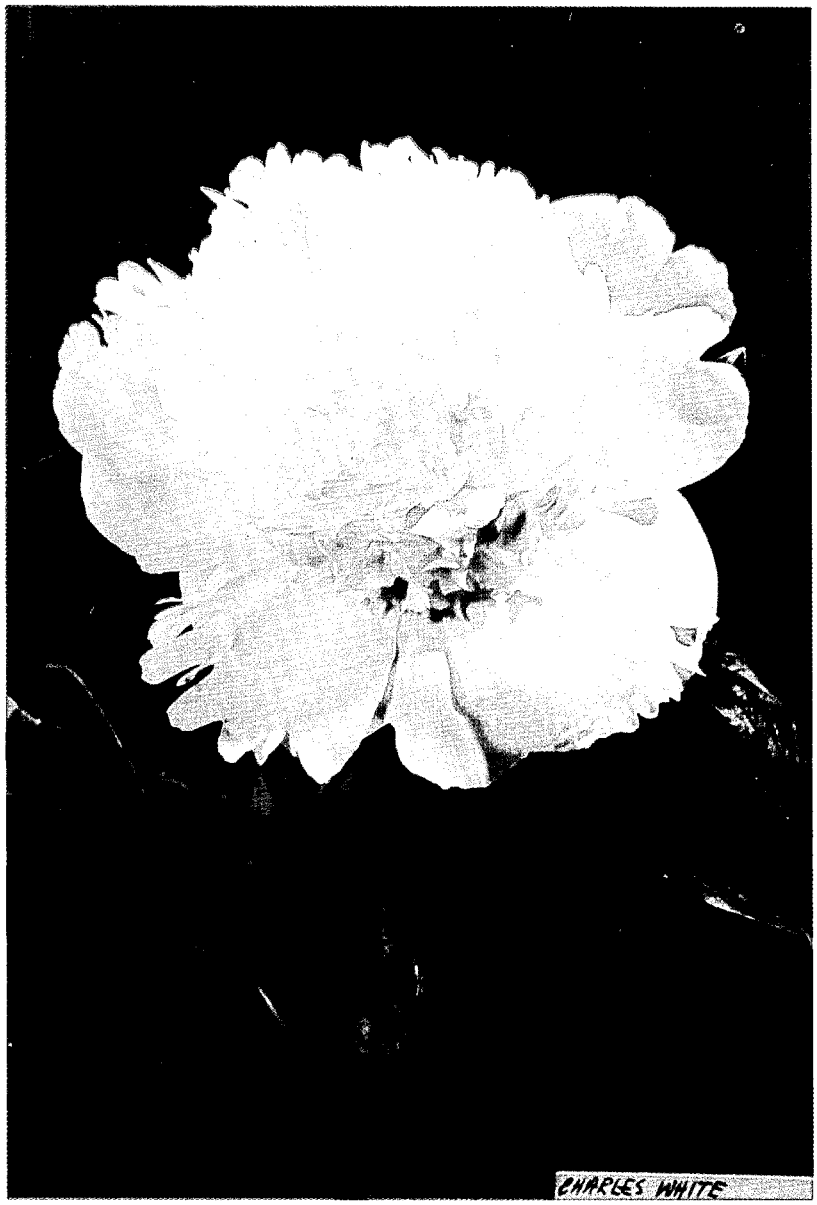

United States Patent

Plant Pat. 3,684

Patented Feb. 11, 1975

3,684

PEONY PLANT

Carl George Klehm, Arlington Heights, Ill., assignor to Klehm Properties, Inc., Arlington Heights, Ill.

Filed Oct. 26, 1973, Ser. No. 410,209

Int. Cl. A01h 5/00

U.S. Cl. Plt.—68 1 Claim

ABSTRACT OF THE DISCLOSURE

A new variety of peony plant distinguished by its profuse production of high quality white blossoms borne on extra long strong stems and possessed of an extremely long lasting quality as a cut flower; and by its early blooming habit which betters that of Mons. Jules Elie, the standard industry early bloomer.

BACKGROUND OF THE NEW PLANT

This new variety of peony plant was discovered by me among nursery field plants at Arlington Heights, Ill., the plant originating as a seedling of Mons. Jules Elie (unpatented) resulting from natural and uncontrolled open field pollination from an unknown pollen source. I selected this plant for propagation and testing because of the high quality of whiteness appearing on the mature blooms and because the blooms of the plant were born on extra long, strong stems which would be ideal for cut flower purposes.

Asexual propagation of this new plant by root division has been carried on by me and under my direction, in nursery gardens at Arlington Heights, Ill., for many years and long observation of this variety through many generations has shown that it not only blooms earlier than its seed parent but it also has the vigorous growth habit and the exceptional supporting strength of stem qualities of the seed parent. Furthermore, the flowers of this plant have been observed to have exceptionally excellent lasting qualities as cut flowers and since all of these characteristics have remained true from generation to generation, over a considerable number of years of testing and observation, they are considered to be firmly fixed. Accordingly, the new plant is now undergoing commercial scale propagation, by root division, at production farms in Arlington Heights, Barrington, Champaign and Noble, Ill.

DESCRIPTION OF THE DRAWING

This new variety of peony plant is illustrated by the accompanying full color photographic drawing which shows the flower at an early stage of full bloom. The flower coloration shown is believed to be as nearly true as it is reasonably possible to obtain by conventional professional photographic standards and procedures.

DESCRIPTION OF THE PLANT

The following is a detailed description of my new variety of peony plant with color specification according to The RHS Colour Chart produced with collaboration of the British Colour Council and published by The Royal Horticultural Society of London, England, the observations having been made at Arlington Heights, Ill.

The Plant

Origin: Seedling.

Parentage:

*Seed parent.*—Mons. Jules Elie (unpatented).

*Pollen parent.*—Unknown. Pollination of the seed parent occurred through natural, uncontrolled, open field pollen transference.

Classification: *Paeonia lactiflora.*

Form: Multi-stem bush.

Height: 42 to 48 inches.

Growth: Vigorous, upright and exceptionally strong. Stem size: ½ to ¾ inch diameter at base.

Foliage: Quantity—Abundant. 5 leaflets per stem.

*Leaf size.*—Large.

*Leaf shape.*—Elliptically acute with smooth margins.

*Aspect.*—Glossy.

*Ribs and veins.*—Pronounced.

*Rachis.*—Normal.

*Color.*—Upper side—Forest Green—Green Group 135A. Under side—Almond Green—Green Group 135B.

The Bud

Size: Medium.

Form: Globular and smooth.

Opening rate: Varies, depending on climate conditions.

Color:

*When sepals first divide*—Cream-White—Yellow-White Group 158D.

*When petals begin to unfurl*—Cream to White.

Sepals: Hooded over and tightly wrapped around the bud.

Color:

*Inside*—Limpid Green—Green Group 135D.

*Outside*—Medium Green—Green Group 135C.

The Flower

Blooming habit: This plant blooms profusely, once each year in spring and at least two days before the industry standard early bloomer (Mons. Jules Elie).

Borne: Singly with a few axillary buds on each stem.

Size: Medium.

*Diameter.*—About 7 to 7½ inches.

*Depth.*—About 3¼ to 3½ inches.

Shape: Cup-shaped with high center when bloom first opens, changing later to "bomb" type of peony flower.

Petalage: Arrangement—Imbricated.

*Form.*—Spatulate, with notched guard petals.

*Color.*—Outer Petals: Body—White. Base—Cream-White. Yellow-White Group 158D. Inside Petals: Same as outer. Reverse Side: White, with no variegations.

*Texture.*—Soft.

*Appearance.*—Satiny.

*Persistence.*—Petals stay on stem 10 to 16 days, then drop off completely.

Petaloids: None.

Discoloration: Flower fades to pure white after maturity.

Fragrance: Mild peony.

Disease resistance: No root disease noted. This plant has average resistance to Botrytis as observed at production farms in Arlington Heights, Barrington, Champaign and Noble, Ill.

Lasting quality:

*On plant.*—Above average.

*As a Cut Flower.*—Approximately 9 days.

Reproductive Organs

Stamens: None.

Pistils: 3 in number.

Styles: ¾ to 2¼ inches long depending on time of conception.

Fruit

Fertility: The fruit is fertile.

Shape: Generally round.

Color at maturity: Beech Brown 165A.

This new variety of peony plant most nearly resembles the variety Snow Mountain (unpatented). The new plant is particularly distinguished, however, by many outstanding and valuable characteristics, among which are:

A. The extreme earliness of flowering;

B. The extra long flowering stems, often 40 to 50% longer than other cut flower varieties;

C. The desirable and high quality of whiteness of mature blooms;

D. The best lasting quality, as a cut flower, found in a peony plant in more than sixty years of peony plant culture carried on by my family; and E. The aura of elegance surrounding the flowers of this new variety when they are used artistically in formal arrangements.

I claim:

1. A new and distinct variety of peony plant substantially as herein shown and described, characterized by the bomb shape of its white flower, interspersed with an inner blush of yellow before maturity, the earliness of flowering, the long lasting quality as a cut flower, and the extra long length of its flowering stems.

References Cited

UNITED STATES PATENTS

P.P. 2,451 11/1964 Klehm ---------- Plants—68

ROBERT E. BAGWILL, Primary Examiner